(12) United States Patent
Hathorn

(10) Patent No.: US 12,390,386 B2
(45) Date of Patent: Aug. 19, 2025

(54) ENDOSCOPY BAND WITH VISUAL INDICATOR TO ASSIST PLACEMENT

(71) Applicant: ColoWrap, LLC., Durham, NC (US)

(72) Inventor: James Hathorn, Durham, NC (US)

(73) Assignee: ColoWrap, LLC., Durham, NC (US)

( * ) Notice: Subject to any disclaimer, the term of this patent is extended or adjusted under 35 U.S.C. 154(b) by 1042 days.

(21) Appl. No.: 17/180,676

(22) Filed: Feb. 19, 2021

(65) Prior Publication Data

US 2021/0177685 A1 Jun. 17, 2021

Related U.S. Application Data

(63) Continuation-in-part of application No. 16/818,877, filed on Mar. 13, 2020, now Pat. No. 11,701,286, (Continued)

(51) Int. Cl.
*A61F 13/14* (2006.01)
*A61B 17/00* (2006.01)
(Continued)

(52) U.S. Cl.
CPC ............ *A61H 1/008* (2013.01); *A61B 90/17* (2016.02); *A61F 5/0009* (2013.01); *A61F 5/03* (2013.01);
(Continued)

(58) Field of Classification Search
CPC .. A61F 5/03; A61F 5/0009; A61F 5/26; A61F 5/30; A61F 13/148; A61F 5/028;
(Continued)

(56) References Cited

U.S. PATENT DOCUMENTS 3,115,879 A 12/1963 Kaplan
3,120,846 A 2/1964 Fletcher
(Continued)

FOREIGN PATENT DOCUMENTS

CN 202161367 U 3/2012
GB 2381732 A 5/2003
(Continued)

OTHER PUBLICATIONS

European Search Report corresponding the European Patent Application No. 12864172.7, dated Sep. 2, 2015.
(Continued)

*Primary Examiner* — Diane D Yabut
(74) *Attorney, Agent, or Firm* — Procopio, Cory, Hargreaves & Savitch LLP

(57) ABSTRACT

An endoscopy support apparatus that includes a primary wrap sized for placement around a subject's lower abdomen. At least one elastic strap extends from the primary wrap and is configured to extend across at least a portion of the primary wrap and to fasten to a third portion of the primary wrap to adjust the amount of pressure applied by the endoscopy support apparatus. The endoscopy support apparatus includes at least one visual indicator provided on the primary wrap or the at least one elastic strap that indicates placement of the endoscopy support apparatus relative to the subject or adjustment of the at least one elastic strap.

21 Claims, 12 Drawing Sheets

Related U.S. Application Data which is a continuation of application No. 15/256,019, filed on Sep. 2, 2016, now Pat. No. 10,624,808, which is a continuation-in-part of application No. 14/575,860, filed on Dec. 18, 2014, now Pat. No. 10,441,222, which is a continuation-in-part of application No. 13/344,715, filed on Jan. 6, 2012, now Pat. No. 9,724,225.

(60) Provisional application No. 62/978,797, filed on Feb. 19, 2020, provisional application No. 62/214,747, filed on Sep. 4, 2015, provisional application No. 61/944,658, filed on Feb. 26, 2014, provisional application No. 61/917,469, filed on Dec. 18, 2013.

(51) Int. Cl.
| | |
|---|---|
| *A61B 90/17* | (2016.01) |
| *A61F 5/00* | (2006.01) |
| *A61F 5/03* | (2006.01) |
| *A61F 5/30* | (2006.01) |
| *A61H 1/00* | (2006.01) |
| *A61F 5/26* | (2006.01) |

(52) U.S. Cl.
CPC .............. *A61F 5/30* (2013.01); *A61F 13/148* (2013.01); *A61B 2017/00818* (2013.01); *A61F 5/26* (2013.01); *A61H 2205/083* (2013.01)

(58) Field of Classification Search
CPC ............ A61B 90/17; A61B 2090/0811; A61B 17/1322; A61H 1/008; A61H 2205/083
See application file for complete search history.

(56) References Cited

U.S. PATENT DOCUMENTS

| | | | |
|---|---|---|---|
| 3,554,190 A | 1/1971 | Kaplan | |
| 3,902,503 A | 9/1975 | Gaylord, Jr. | |
| 3,920,008 A * | 11/1975 | Lehman | A61F 5/03 602/19 |
| 4,833,730 A | 5/1989 | Nelson | |
| 4,991,234 A | 2/1991 | Greenberg | |
| 5,188,585 A | 2/1993 | Peters | |
| 5,310,401 A | 5/1994 | Striano | |
| 5,464,412 A | 11/1995 | Budding | |
| 5,489,260 A | 2/1996 | Striano | |
| 5,647,824 A | 7/1997 | Levenson | |
| 5,685,321 A * | 11/1997 | Klingenstein | A61F 5/445 128/845 |
| 5,741,295 A * | 4/1998 | McEwen | A61B 17/135 606/202 |
| 5,820,575 A | 10/1998 | Cabrera et al. | |
| 5,885,230 A | 3/1999 | Cherry | |
| 6,503,215 B1 * | 1/2003 | Reinhardt | A61F 5/028 602/41 |
| 6,672,311 B2 | 1/2004 | Rindfleis | |
| 7,074,177 B2 | 7/2006 | Pickett et al. | |
| 8,066,657 B2 | 11/2011 | Frazer | |
| 2002/0108617 A1 | 8/2002 | Rindfleis | |
| 2009/0171259 A1 * | 7/2009 | Soerensen | A61F 13/148 602/61 |
| 2010/0042031 A1 * | 2/2010 | Anglada | A61F 13/102 602/62 |
| 2011/0087263 A1 | 4/2011 | Arber | |
| 2011/0144551 A1 * | 6/2011 | Johnson | A61F 5/028 602/19 |
| 2013/0110019 A1 | 5/2013 | Hopman et al. | |
| 2013/0172671 A1 | 7/2013 | Rentschler et al. | |
| 2013/0178893 A1 | 7/2013 | Hathorn | |
| 2014/0142616 A1 | 5/2014 | Smith | |
| 2014/0323802 A1 | 10/2014 | Lloyd | |
| 2017/0035425 A1 | 2/2017 | Fegelman et al. | |
| 2019/0274687 A1 | 9/2019 | Wang et al. | |

FOREIGN PATENT DOCUMENTS

| | | | |
|---|---|---|---|
| JP | 3051938 U | 6/1998 | |
| JP | 2005-021113 A | 1/2005 | |
| JP | 2006-314711 A | 11/2006 | |
| KR | 200264387 Y1 | 2/2002 | |
| WO | 9508308 A1 | 3/1995 | |
| WO | 9614811 A1 | 5/1996 | |
| WO | 9746180 A1 | 12/1997 | |
| WO | WO-2015095558 A1 * | 6/2015 | ......... A61B 1/00131 |

OTHER PUBLICATIONS

International Search Report and Written Opinion of related International Patent Application No. PCT/US2014/071218, dated Mar. 24, 2015.

Soper, Nathaniel J., et al., "Chapter 45: Flexible Endoscopy of the Lower Gastrointestinal Tract, Endoscopic and Laparoscopic Surgery", Lippinscott Williams & Wilkins, Philadelphiam PA, 2009, pp. 451.

Non-Final Office Action in U.S. Appl. No. 17/972,581, mailed Feb. 18, 2025. 26 pages.

* cited by examiner

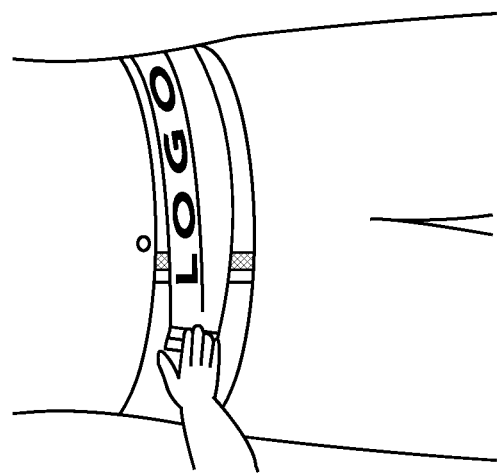
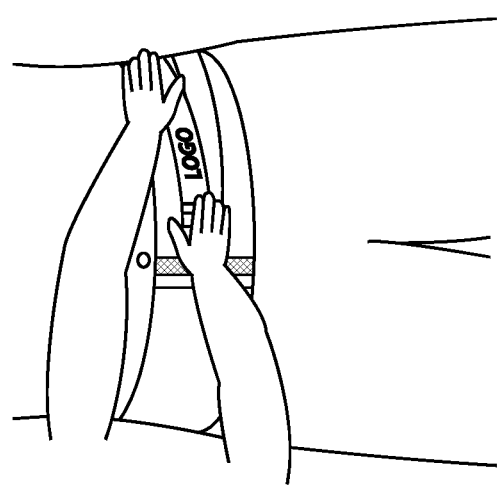
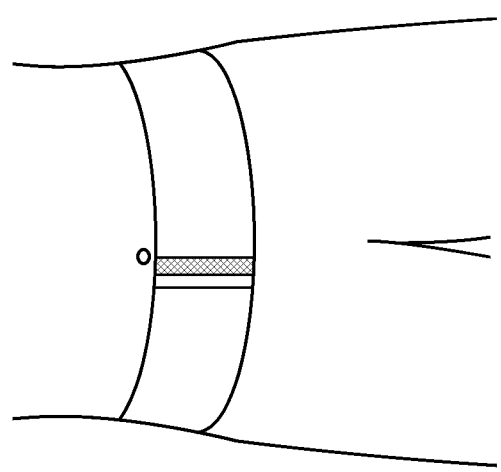
FIG. 4

ENDOSCOPY BAND WITH VISUAL INDICATOR TO ASSIST PLACEMENT

CROSS REFERENCE TO RELATED APPLICATIONS

This application is a continuation-in-part of U.S. application Ser. No. 16/818,877, entitled Endoscopy Band with Sigmoid Support Apparatus, and filed on Mar. 13, 2020, which is a continuation of U.S. application Ser. No. 15/256,019, entitled "METHOD AND APPARATUS FOR ENHANCED VISUALIZATION DURING ENDOSCOPY," and filed on Sep. 2, 2016, which claims the benefit of priority of U.S. Provisional Application No. 62/214,747, entitled "IMPROVED BOWEL STABILITY AND ENHANCED VISUALIZATION DURING ENDOSCOPY" and filed on Sep. 4, 2015, and is a continuation-in-part of U.S. application Ser. No. 14/575,860, entitled "ENDOSCOPY BAND WITH SIGMOID SUPPORT APPARATUS," and filed on Dec. 18, 2014, which is a continuation-in-part of U.S. application Ser. No. 13/344,715, entitled "METHOD AND APPARATUS FOR TENSILE COLONOSCOPY COMPRESSION," and filed on Jan. 6, 2012, and claims the benefit of U.S. Provisional Application Ser. No. 61/917,469, entitled "COLONOSCOPY BAND WITH SIGMOID SPLINT" and filed on Dec. 18, 2013, and U.S. Provisional Application Ser. No. 61/944,658 entitled "ENDOSCOPY BAND WITH SIGMOID SUPPORT APPARATUS" and filed on Feb. 26, 2014, and claims the benefit of U.S. Provisional Application Ser. No. 62/978,797, entitled "Endoscopy Band With Visual Indicator to Assist Placement" and filed on Feb. 19, 2020, the contents of each of which are expressly incorporated by reference herein in its entirety.

BACKGROUND

A colonoscopy is an examination of the large intestine or colon through the use of a colonoscope. A colonoscope is a flexible, tube-like inspection device having a camera at its end. Colonoscopies are performed for a variety of medical reasons including detection of inflamed tissue, ulcers, abnormal growths or polyps, and colorectal cancer. Colonoscopy is increasingly used as a screening tool to detect colorectal cancer.

During a colonoscopy, a colonoscope is inserted into a patient's rectum and then advanced to the beginning of the colon (an area known as the cecum) in order to examine the lining of the large intestine. The efficiency and accuracy of this procedure is largely dependent on the ease with which the colonoscope can be advanced. During the procedure, the colon may become over-distended or flopped in unnatural directions creating loops that hinder the advancement of the colonoscope and resulting in patient discomfort, longer examination times, and potentially inaccurate or incomplete screenings.

Currently, the difficulty in advancing the scope is addressed by the application of manual pressure by a technician to manually support the patient's colon. The application of manual pressure is time-consuming and varies depending on the particular technician's strength, technique, endurance, and training. In order to apply differential pressure, the technician may roll the patient from the left side to a supine or to a prone position, which can be a difficult task with a sedated patient. The application of manual pressure and movement of the patient in order to support the patient's colon and advance the colonoscope during the procedure places a physical toll on the technician.

SUMMARY

In an aspect of the disclosure, a method and apparatus for applying pressure to the abdomen of a patient is provided to ease the passage of an endoscope during procedures used to examine the bowels including colonoscopy, sigmoidoscopy, and enteroscopy. Aspects presented herein exert both broad, uniform lower abdominal pressure as well as additional, location-specific pressure upon the sigmoid colon for the purposes of preventing and reducing intestinal looping, eliminating the need for the application of manual pressure, improving patient safety, comfort, and satisfaction, and preventing musculoskeletal injury to endoscopy healthcare providers.

Aspects include a primary wrap sized for placement around a subject's lower abdomen and at least one secondary strap extending from the primary wrap and configured to extend across at least a portion of the primary wrap and to fasten to a third portion of the primary wrap to adjust the amount of pressure applied by the endoscopy support apparatus. A visual guide is provided on the primary wrap and/or the at least one secondary strap to provide visual assistance to the technician in properly placing the device on a patient and adjusting focused support using the secondary strap.

Additional advantages and novel features of aspects of the present invention will be set forth in part in the description that follows, and in part will become more apparent to those skilled in the art upon examination of the following or upon learning by practice thereof.

BRIEF DESCRIPTION OF THE DRAWINGS

FIG. 4 illustrates a method of use of an endoscopy band device with an elastic secondary strap capable of retaining tension and exerting directed force for an endoscopy procedure.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

Aspects presented herein comprise a primary abdominal wrap that is secured around the lower abdomen of the patient and a secondary strap that provides directed force and support to the sigmoid colon. When the device is securely fastened, the secondary strap may be adjusted to serve as a focused support or 'splint' for the sigmoid colon. The apparatus further includes visual guides or indicators that provide visual reference marks and guidance for placing the apparatus on a patient and/or for adjusting directed force using the secondary strap.

Figure 1C:
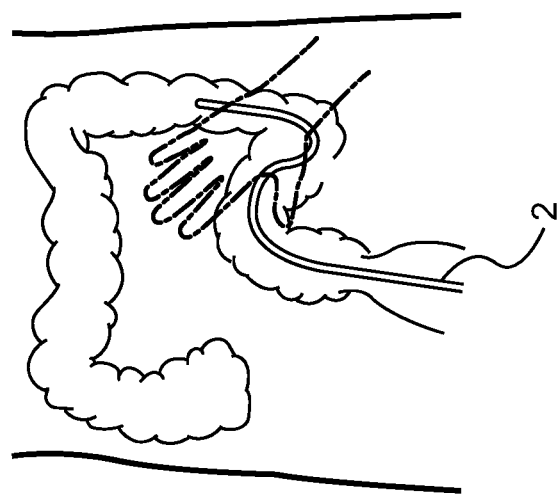
FIG. 1C is a schematic view of a colon showing the application of manual pressure to the colon to facilitate insertion of an endoscope.
Figure 1B:
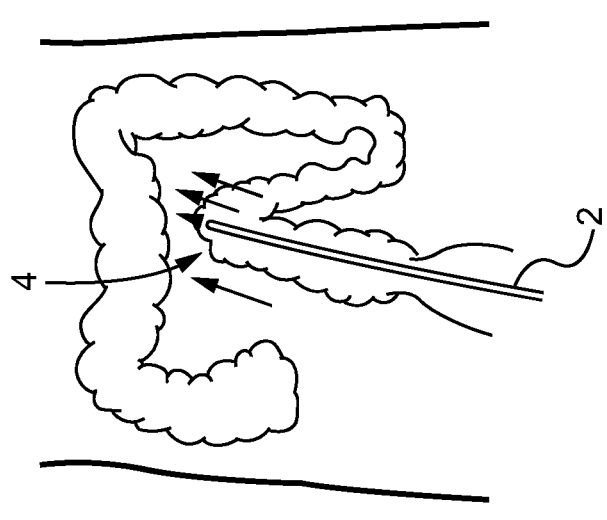
FIG. 1B is a schematic view of a colon in which a sigmoid loop has developed due to an attempt to advance the endoscope against an unsupported colon wall.
Figure 1A:
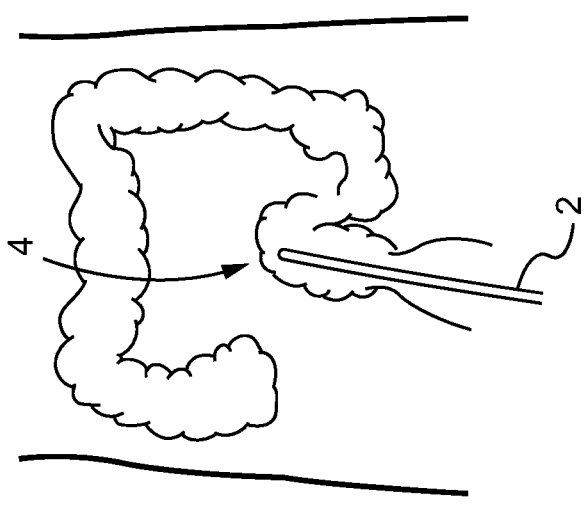
FIG. 1A is a schematic view of a colon with an endoscope (also known as a colonoscope for colonoscopy procedures) partially inserted therein.

FIGS. 1A-1C, illustrate a sequence of steps of a colonoscopy. In FIG. 1A, a colonoscope 2 is inserted into the patient's rectum and advanced forward through the length of the colon. As the operator passes the colonoscope through the sigmoid region of the colon 4, the colonoscope may become impinged and cause distention and looping of the anatomy, as shown in FIG. 1B. The distention causes discomfort to the patient and increases the time required for the colonoscopy. In order to reduce the distended or looped area, a technician may apply manual pressure to abdomen of the patient. Among other examples, the technician may be a nurse, assistant, or other staff member. For example, the pressure may be applied by a nurse or surgical assistant as shown in FIG. 1C.

The application of manual pressure is time-consuming and places a physical toll on the technician. The effectiveness of the manual pressure varies depending on the particular technician's strength, technique, endurance, and training. In order to apply differential pressure, the technician may roll the patient from the left side to a supine or to a prone position, which can be a difficult task with a sedated patient. The application of manual pressure and movement of the patient in order to support the patient's colon and advance the colonoscope during the procedure places may even lead to injury of the technician.

Many patients undergo colonoscopy while placed in the left lateral decubitus position on the stretcher or operating table. Additional information about the use of such manual pressure can be found in Prechel J A, Hucke R. Safe and effective abdominal pressure during colonoscopy: forearm versus open hand technique. Gastroenterol Nurs 2009; 32:27-30; quiz 31-2, the entire contents of which are incorporated herein by reference. In applying manual pressure, the technician may reach over the patient from the opposite side of the table and to deploy pressure by placing their hands against the patient's sigmoid colon and then leaning backwards, using their bodyweight for leverage to exert force. While these methods are generally effective at generating pressure, they have also been identified as a causative factor for the high rate of work-related injuries among endoscopy nurses and staff. Physicians performing colonoscopy suffer work-related musculoskeletal injury at a particularly high-rate as well. The most frequent site of physician injury is the right upper extremity which experiences peak torque forces when while operators are attempting to advance the scope through (a looping) sigmoid colon. Additional details can be found in Spanarkel M, Hathorn J P. Looping During Colonoscopy: A Major, Implied Cause of Injury Among Endoscopy Healthcare Providers and a Proposed Solution, 2013, the entire contents of which are incorporated herein by reference.

Aspects described herein may similarly be applied for other endoscopic procedures such as sigmoidoscopy and retrograde enteroscopy procedures. Sigmoidoscopy is an examination of only the lower part of the colon, from the anus to the descending colon. An endoscope is inserted into the lower part of the colon. Enteroscopy is an examination of the small bowel. During retrograde enteroscopy, an endoscope is inserted in the anus and passed through the colon and the cecum and into the small bowel. Successfully navigating the loop-prone sigmoid region is necessary to complete both sigmoidoscopy and retrograde enteroscopy and thus aspects described herein can be used to help facilitate colonoscopy, sigmoidoscopy, retrograde enteroscopy, and other endoscopic procedures.

Figure 2:
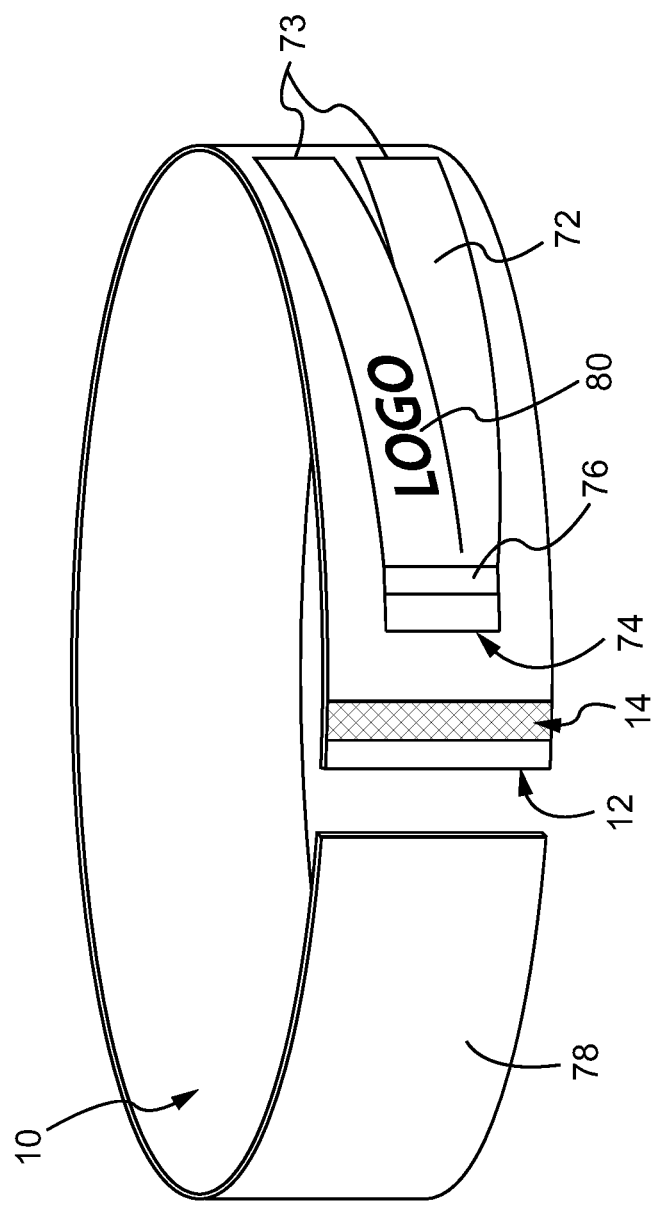
FIG. 2 is an illustration of an unfastened endoscopy band device with an elastic secondary strap capable of retaining tension and exerting directed force to the colon, including the sigmoid, traverse, and cecal regions, stretched and fastened to the primary wrap.
Figure 5:
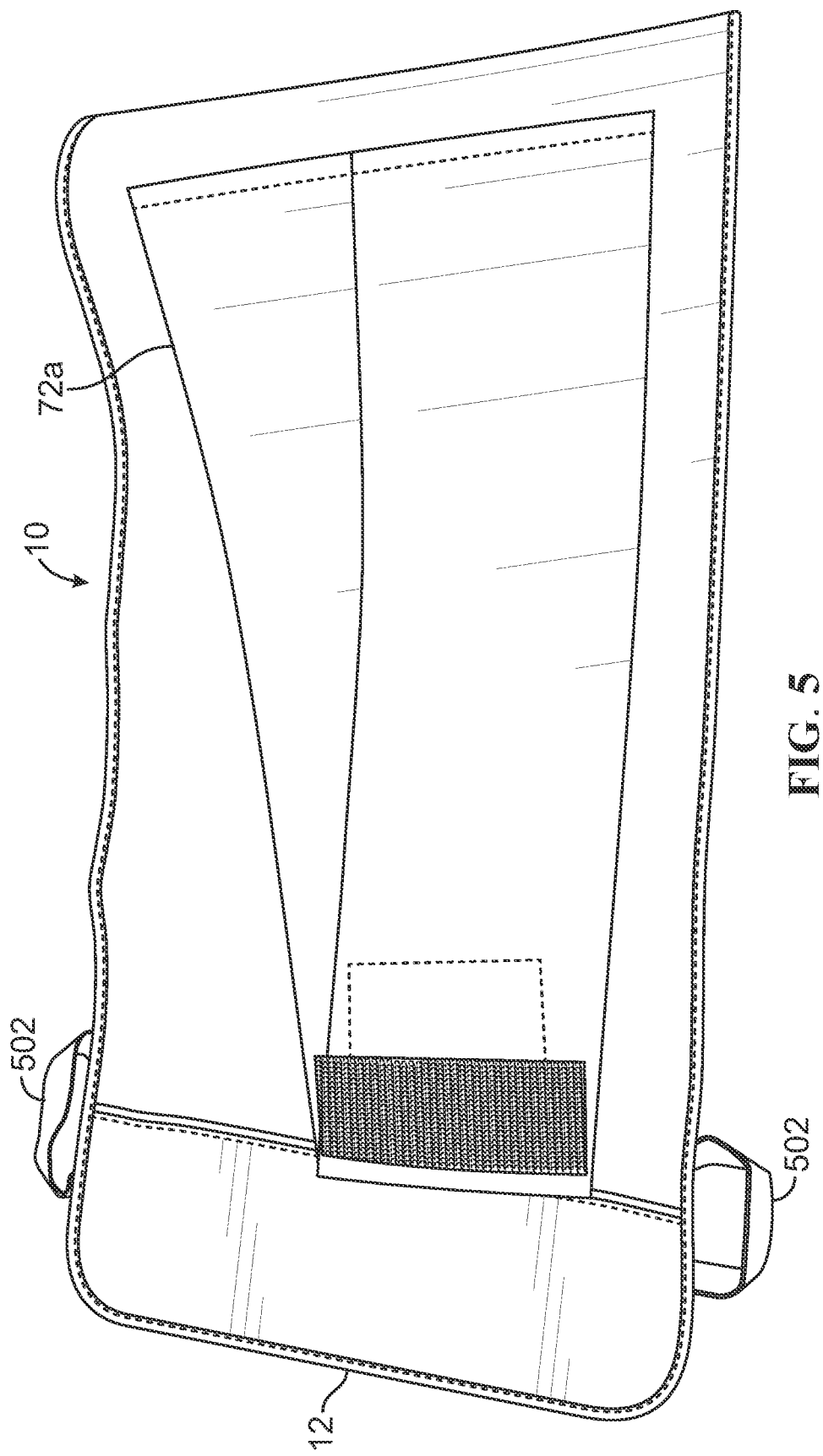
FIG. 5 is an illustration of a portion of an endoscopy band showing a tapered secondary strap.

FIG. 2 illustrates an example device including a primary elongated band or wrap 10 of sufficient length for placement around a patient's lower abdomen. A closing mechanism 12 may be provided at the end of the primary band to secure the device around the patient so that it provides the desired amount of broad support and compression. A handle 14 may be sewn onto the exterior of one or both ends of the primary wrap to assist in fastening and closure. FIG. 5 illustrates a portion of an example wrap 10 having handles 502 provided at an end of the wrap 10. The handles may be used by the technician to stretch the wrap and apply a desired degree of compression when fastening the primary wrap 10 around the patient.

The primary wrap 10 may have a circumferential length between approximately 15 and 75 inches in order to accommodate varying abdominal girths in patients. The width of the primary wrap 10 may be between 6 and 10 inches, although variations having widths of between 3 and 20 inches may be used depending on the size of the patient and to accommodate special circumstances such as an abdominal hernia or a large pannus. For example, the primary wrap may be configured to have a width that allows it to be fastened around the patient's lower abdomen with the upper edge of the wrap just below the umbilicus, or near the umbilicus, and the bottom edge of the wrap along or close to the pubic line. The width of the primary wrap may be selected so as not to be so large that the upper edge conceals the umbilicus and additional areas of the abdomen above the umbilicus. This configuration may be made in order to avoid pressure on the diaphragm or stomach, as pressure on the diaphragm and stomach during colonoscopy can increase the risk of oxygen deprivation and aspiration events, respectively, due to the fact that the patient is generally sedated during the procedure. The primary wrap 10 may comprise, entirely or in part, a flexible, bio-compatible foam, rubber, neoprene, polyester, nylon, non-woven or woven fabric, mesh fabric, synthetic fabric, microfiber fabric, silicon or vinyl plastic, or any other materials generally known to be used in medical fabrics and goods. The primary wrap 10 may be composed of both elastic and inelastic materials. In one example, the primary wrap 10 may comprise multiple layers laminated together. For example, the primary wrap 10 may comprise a neoprene layer and an outer fabric layer laminated on the neoprene layer. The fabric layer may enable the secondary strap to be removably fastened along the length of the primary wrap and may also enable visual indicators to be printed on the fabric, such as a nylon loop fabric. The primary wrap may also comprise an inner layer laminated on the neoprene. The inner layer may comprise a fabric or other material that is selected for skin sensitivity. For example, the inner layer may comprise a fabric or other material that is latex free, biocompatible, and/or skin sensitive. The inner layer may be the layer that is applied against the skin of the patient. In some aspects, the primary wrap may comprise 3D spacer fabrics, which may provide compression, elasticity, cushioning, breathability, air permeability, thermal insulation, temperature regulation, flexibility with resistance to bending/rolling, good draping, adjustable vapor transport, good aging qualities, surface and wash resistance, sterilization capabilities, and diverse surface design capabilities. A 3D spacer fabric may comprise a manufactured textile structure in which two fabric layers are connected by a layer of pile threads, which may be referred to as pile yarns.

The primary wrap may comprise two or more sections that vary in material type. In one example, a first set of one or more sections may be composed of a flexible, elastic or semi-elastic, medium-thickness, latex-free neoprene with thin polyester or nylon glued to its interior and exterior sides. Among others, this material may be capable of providing broad, firm, yet comfortable support to the patient's abdominal region. Another set of one or more sections of the primary wrap 10 may comprise a relatively inelastic material, such as a woven fabric. The inelastic section may be provided at the location into which or under which an insert is placed. Upon deployment of the device, the inelastic section may be positioned in the patient's lower left abdominal quadrant, over the sigmoid region.

For the primary wrap to provide appropriate general compression and support, it may be important that the wrap remain flat against the body when fastened around the abdomen. This is notable because certain materials and designs have a tendency to roll-up when stretched or wrapped around the abdomen, particularly when the device is being applied to patients with a large pannus. To prevent roll-up from occurring, aspects of the invention may include reinforcements to ensure that the primary abdominal wrap remains flat against the body when used in patients of varying body sizes. This may be accomplished by the application of serge stitching along the edges of the primary abdominal band.

The primary wrap may also accommodate an insert or attachment that provides specific support to one or more areas of the colon including the sigmoid, transverse, and cecal regions as well as the splenic and hepatic flexures. When the device is securely fastened, the secondary strap, the insert, or both, may be pushed, pulled, or otherwise pressed into the body in a manner that serves to support or 'splint' one or more areas of the colon including the sigmoid, transverse, and cecal regions as well as the splenic and hepatic flexures. Aspects described herein may be designed to provide broad lower abdominal support, and additional direct force to one or more areas of the colon including the sigmoid, transverse, and cecal regions as well as the splenic and hepatic flexures of a patient undergoing colonoscopy.

The primary wrap 10 may be placed around the patient's lower abdomen and secured using a closing mechanism 12 consisting of a strip of VELCRO® or hook material 13 placed on the interior of the wrap 10 close to the location of the handle 14 on the opposite side. This hook strip 13 may be fastened to the exterior side of the opposite end of the primary wrap 10.

The edges of the hook strip 13 might not extend to the edges of the primary wrap 10. This construction may be designed to minimize the chance that the hook strip 13 comes into contact with the patient's skin, or with the gloves of the nurse or assistant deploying the device, as there is a small but known risk of VELCRO®, or a hook and pile material, being capable of tearing medical gloves.

An additional feature designed to reduce the likelihood of patient and provider contact with the hook material. In aspects incorporating this feature, prior to the device being packaged, a thin layer of material may be applied to hook strips that are incorporated into the device. This layer may comprise, e.g., paper, plastic, fabric, silicon, or any other biocompatible material typically used in healthcare products. Additionally, the layer may be lightly adhered to the hook strips so that it remains in place—until it is easily removed and disposed of by the end user just prior to the device's application on the patient. This feature may be helpful in use of a secondary strap 72, because it may be helpful for the secondary strap 72 to remain unfastened until the primary wrap 10 is fastened and properly positioned. Having a layer covering the hook strip 75 on the secondary strap 72 helps to ensure that the secondary strap will not be accidentally fastened while the user is securing the primary wrap 10 around the patient's abdomen.

Figure 3:
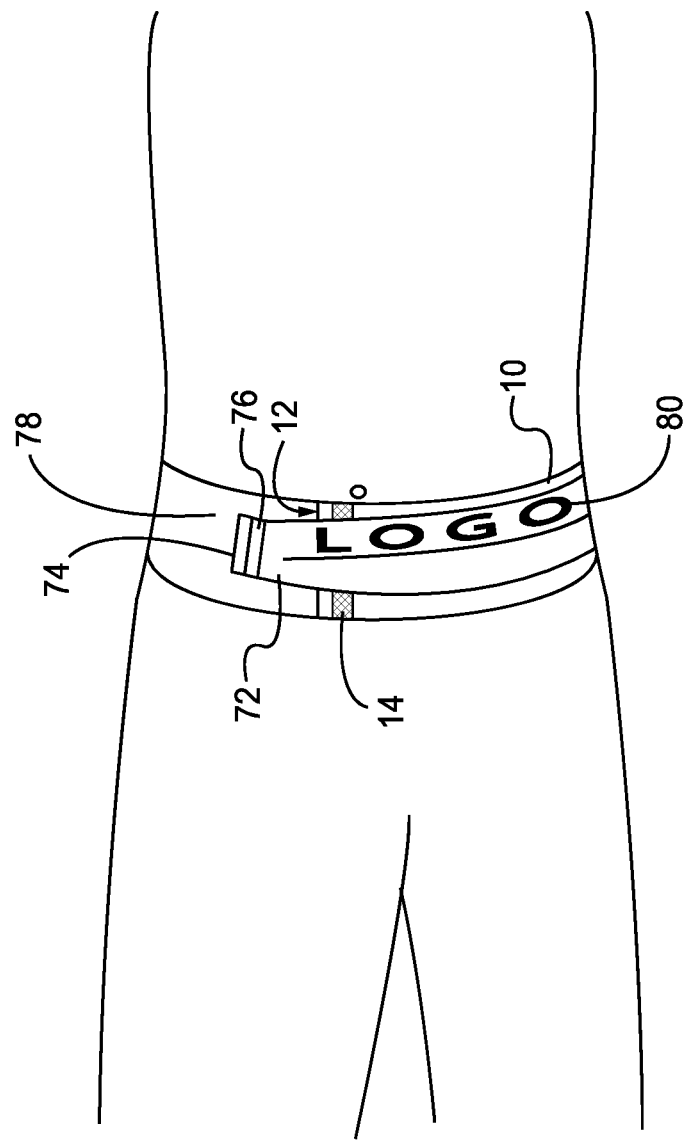
FIG. 3 is a perspective view of the endoscopy band device depicted in FIG. 2 as it appears when applied to a patient, in accordance with aspects of the present invention.
Figure 8:
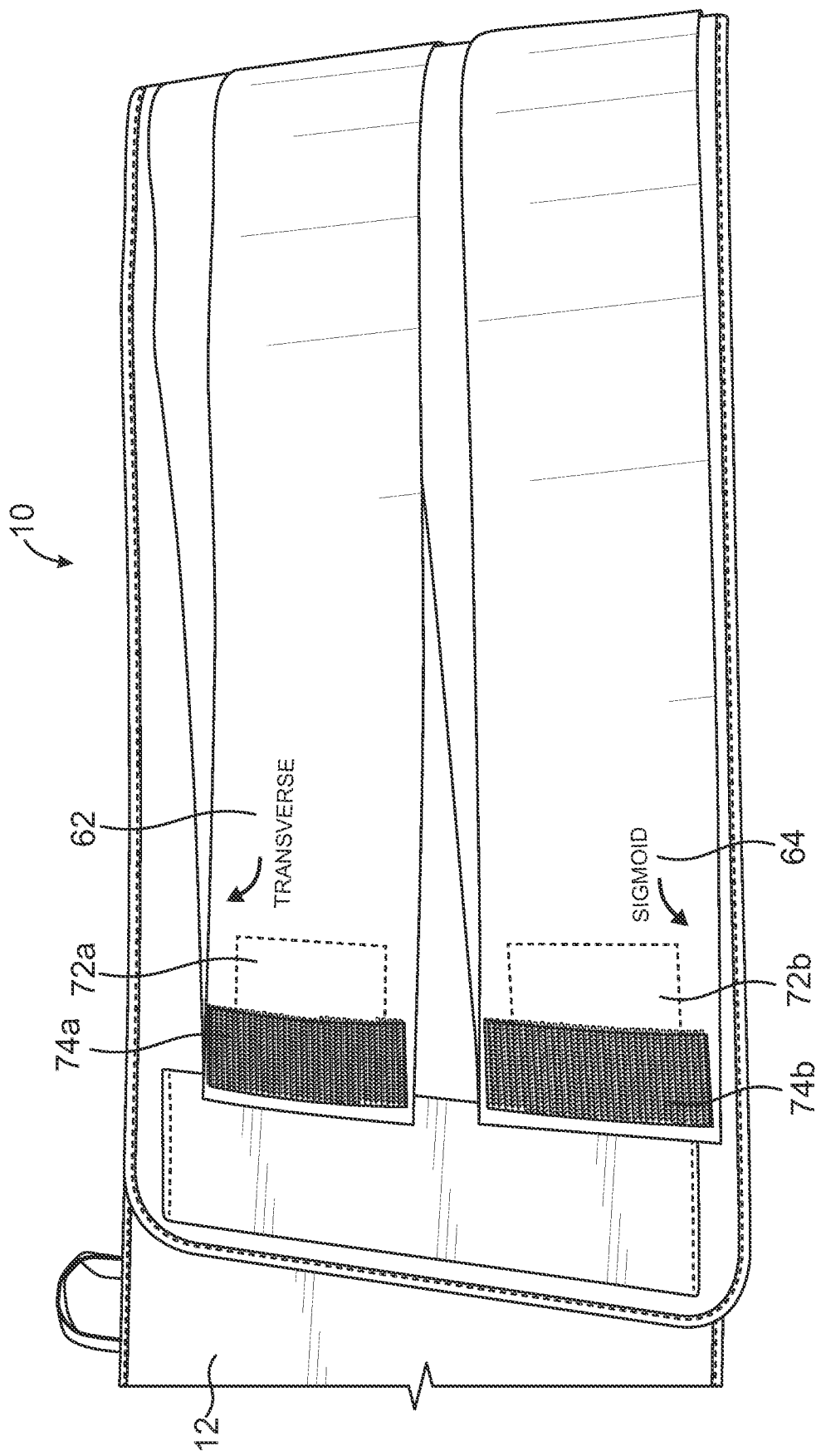
FIG. 8 illustrates an endoscopy band having multiple secondary straps with visual guides for adjusting directional force with the secondary straps.

The addition of one or more appendages on the exterior of the primary wrap facilitates the application of additional directed force, e.g., without requiring adjustment of the primary wrap. The appendages may comprise one, or multiple, straps attached on one side to the edge or edges of non-elastic section. FIGS. 2-4 illustrate an example with a single secondary strap. FIG. 8 illustrates an example having multiple secondary straps 72a, 72b. On the unattached end of these straps, there may be a closing mechanism, e.g., 74a, 74b. The closing mechanism may include a handle or loop near the end of the strap, that may provide greater ease to a technician, or added security, in pulling the elastic strap to apply targeted, additional compression. The straps 72a, 72b may be pulled horizontally along the exterior of the primary wrap, and fastened using the closing mechanism securely enough to maintain tension. The one or more straps may comprise an elastic material that is configured to be stretched and fastened to the primary wrap in order to apply targeted compression through elastic contraction of the material. The amount of targeted compression may be adjusted through adjustment of the position at which the removable end is coupled to the primary wrap, such as through a Velcro fastener. In some examples, the straps may be secured to an inelastic section of the primary wrap, and the tension generated by fastening these straps may cause additional compression of the inelastic section and/or an insert toward the body of the patient.

As depicted in FIG. 4, the secondary strap 72 may allow nurses and technicians to easily adjust and readjust the force on a particular region of the patient's abdomen, such as the sigmoid colon and/or the transverse colon, from the location in the procedure or operating room that these staff members typically occupy, relative to how patients are often positioned during an endoscopy procedure. The endoscopy compression device described herein additionally eliminates the need for the nurse or assistant to provide manual abdominal compression, thereby reducing their risk of musculoskeletal injury. Additional, manual compression may be applied along with compression from the device. The device is designed to be quickly and easily removed should the need arise.

The secondary strap 72 may be coupled, e.g., sewn, to a portion of the wrap that is configured for placement over a left side of the patient's lower abdomen. The portion of the secondary strap 72 that is coupled to the primary wrap may be referred to as the secured end and may be non-removably coupled to the strap, such as sewn or formed as an extension of the primary wrap material. The strap can be configured to be pulled from left to right, e.g., to stretch across the lower abdomen and/or left lower abdominal quadrant from the left side of the patient's body towards right side of the patient's body. This placement of the secondary strap 72 may enable the compression to be easily adjusted as the patient lies on their left side during the procedure. As the strap pulls from left to right across the lower abdomen, additional leverage and compression may be generated by the patient's body when the strap is in place. As the strap stretches from left to right cross the patient's abdomen, the level of compression generated by the device can easily be adjusted during the procedure, e.g., while the patient is lying on their left side.

In some aspects, the secured end of the strap 72 may be connected to the wrap 10 in a manner that the secured end of the strap is under the patient during a procedure.

As illustrated in FIGS. 2-4, the device may include a primary wrap 10, with a closing mechanism 12, and at least one handle 14 to assist in fastening the primary wrap around the patient's lower abdomen. The device may also include a secondary strap 72 attached to the exterior side 78 of the primary wrap 10, with a closing mechanism 74 that allows the strap, e.g., to be fastened to the exterior side 78 of the primary wrap 10. In an aspect, the closing mechanism 74 of the secondary strap 72 may comprise a hook strip 75 on the inside of the secondary strap 72 that is capable of fastening anywhere along the exterior side 78 of the primary wrap 10. In this example, the exterior side 78 of the primary wrap 10 may comprise a hook-compatible material to which the hook strip 75 can be fastened and remain fastened while the secondary strap is stretched and under tension. The secondary strap 72 may be constructed of an elastic or semi-elastic material that is capable of retaining tension when stretched horizontally and fastened to the exterior side 78 of the primary wrap 10 using the closing mechanism 74. The secondary strap 72 may comprise the same or different materials than the materials comprised in the primary wrap 10. The secondary strap 72 may comprise one or more layers of materials. In an example, the secondary strap 72 may comprise an elastic strap the entire length of which equals approximately twice the intended length of the secondary strap 72. As illustrated, the secondary strap may taper along a length of the strap 72. In the example in FIGS. 2-4, the elastic strap may be doubled-over, and both ends may be sewn to the exterior 78 of the primary wrap 10 along the same vertical line 73, creating the horizontal 'V' appearance of the secondary strap 72. Doubling-over the material composing the secondary strap can serve to increase the breadth and force generated by the secondary strap, while preventing the incurrence of additional materials costs that would be associated with using a taller, single-layered strap instead. The midpoint of the secondary strap may be positioned approximately over the patient's lower left quadrant once it is stretched and fastened. In other examples, such as shown in FIGS. 5, 6, and 8, the secondary strap 72 may be a unitary piece having at least one tapering edge.

Figure 6:
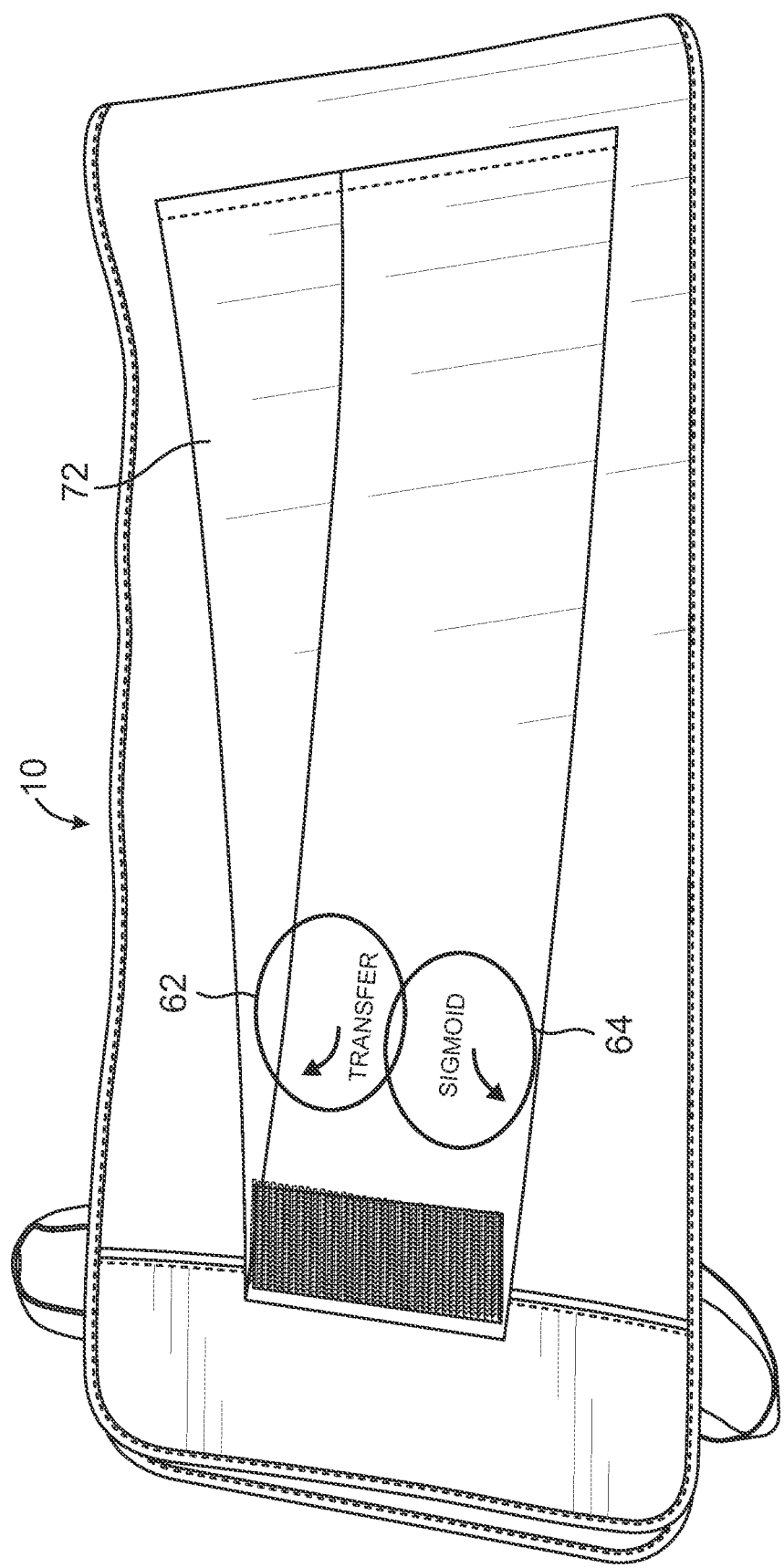
FIG. 6 illustrates a portion of an endoscopy band including visual guides for adjusting directional force with the secondary strap.

FIG. 6 illustrates an example in which a visual guide 60 may be provided on the secondary strap 72 to assist adjustment of the targeted compression or splinting by the secondary strap. A first indicator 62 may indicate the direction in which the secondary strap may be pulled to apply focused compression on the transverse colon. The indicator 62 may include an image, such as an arrow, showing the direction in which the secondary strap 72 is to be stretched, pulled, or moved in order to apply focused pressure on the transverse colon. The indicator 62 may include text that identifies the area of compression or that provides additional assistance in applying the focused pressure. In FIG. 6, the indicator 62 includes an arrow and the text "transverse" that indicates in a simple manner to the technician the way in which the secondary strap is to stretched across the abdomen of the patient and secured to the primary wrap 10 in order to apply focused pressure to the transverse colon. More than one indicator may be provided. For example, FIG. 6 illustrates a second indicator 64 indicating a different direction in which the secondary strap may be pulled to apply focused compression to the sigmoid colon. The indicator 64 may include an image and/or text, similar to the indicator 62. The indicators 62 and 64 in FIG. 6 is merely an example to illustrate the concept, and other images or text description may also be used. Although specific examples have been provided for indicators 62 and 64 for adjustment of targeted compression or splinting of the transverse colon and/or the sigmoid color, indicator(s) may be provided that provide a visual image and/or description that assist in placing the secondary strap 72 to apply compression for other areas involved in an endoscopy procedure, such as the splenic flexure, the hepatic flexure, etc.

As described above, multiple secondary straps may be provided on the device. FIG. 8 illustrates an example on which the indicators 62 and 64 are provided on different secondary straps. For example, the device may include two secondary straps, as shown in FIG. 8. A first elastic strap 72b may extend in the left to right direction from the primary wrap for application of targeted compression to a first abdominal region (e.g., a sigmoid region) of the subject. A second elastic strap may extend from the primary wrap extending in the left to right direction for the application of targeted compression to a second abdominal region of the subject. The primary wrap may include an upper edge for placement relative to an umbilical line of the subject (e.g., such as shown at 172) and a lower edge for placement below the umbilical line of the subject. The first elastic strap and the second elastic strap may extend from the primary wrap at a same position along the length of the primary wrap. For example, the two secondary straps may be sewn (or otherwise fastened or extending) from a same position along a length of the strap. The first strap may be positioned below the second strap along a width of the primary wrap. For example, as shown in FIG. 8, the first elastic strap may extend from a first position along a width of the primary wrap and the second elastic strap may extend from a second position along the width of the primary wrap, the second position being closer to the upper edge than the first position. The use of multiple secondary straps enables a user to simultaneously apply targeted compression of different abdominal areas, e.g., different regions of a colon (such as the sigmoid and/or transverse regions) during an endoscopy procedure. Similarly, having multiple secondary straps enables an adjustment of the targeted compression for one abdominal region while retaining the targeted compression of the other abdominal region. For example, the technician may apply targeted compression using the first and second strap. During an endoscopy procedure, the technician may adjust the first strap without removing or readjusting the second strap.

Figure 7:
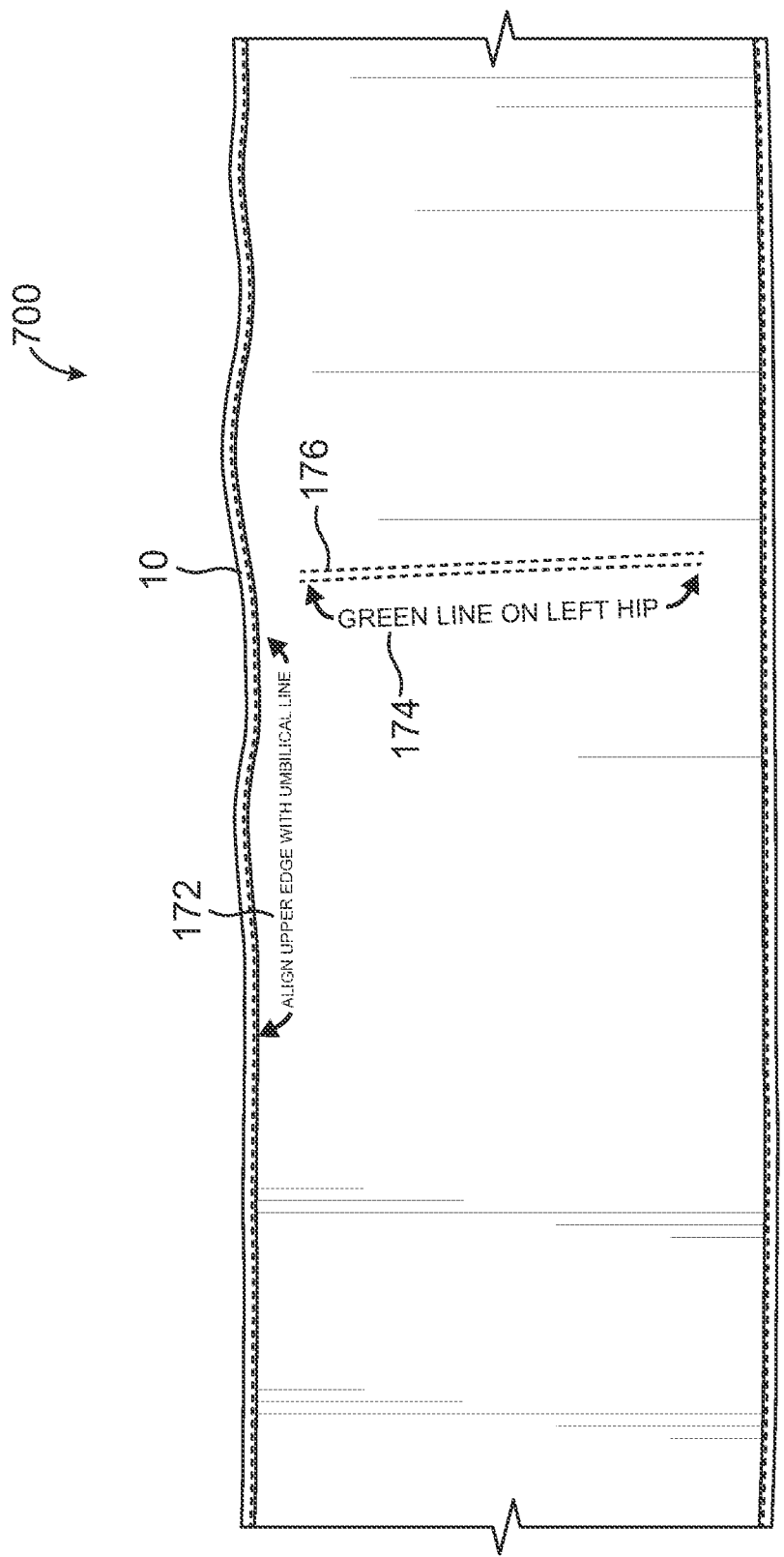
FIG. 7 illustrates an interior of an endoscopy band including visual guides for placement of the band on a patient.

FIG. 7 illustrates an example in which a visual guide or indication may be provided on the primary wrap 10 to assist in placement of the primary wrap on the patient. FIG. 7 illustrates a portion of the primary wrap 10 on a side that is configured for placement against the patient, e.g., which may be referred to as an interior side of the wrap 10. In FIG. 7, a first indicator 172 provides a visual indication to the technician that the correct placement of the device, to assist with an endoscopy procedure, includes aligning the upper edge of the primary wrap 10 with an umbilical line of the patient. The indicator 172 may include an image, such as one or more arrows that show the edge of the wrap 10 to be aligned with the umbilical line of the patient and/or may include text describing the alignment to the technician. For example, in FIG. 7, the text indicates "Align upper edge with umbilical line." The example indicator 172 in FIG. 7 is merely an example to illustrate the concept, and other images or text description may also be used to provide guidance about the placement of the primary wrap relative to the patient. FIG. 7 also illustrates an indicator 174 that provides guidance for placement of the primary wrap 10 on the patient so that the secondary strap is in a position to provide the targeted compression to the sigmoid colon, transverse colon, etc. The indicator 174 may include an image, such as one or more arrows that show the portion of the wrap 10 to be aligned with a left hip of the patient and/or may include text describing the alignment to the technician. For example, in FIG. 7, the text indicates "Green line on left hip." The visual indicator may be used in combination with a visual indication of the end of the secondary strap 172 that is fixed to the opposite side of the primary wrap 10. As illustrated in FIG. 7, the stitching 176 that fixes the end of the secondary strap may use a contrasting color to the primary wrap 10 so that the stitching provides a visual reference for the placement of that section of the primary wrap relative to the left hip of the patient. The example indicator 174 in FIG. 7 is merely an example to illustrate the concept, and other images or text description may also be used to provide guidance about the placement of the primary wrap relative to the patient.

Mechanisms for indicating stretch and compression, such as those described in connection, may be provided so that the device includes a mechanism to visually indicate the magnitude of force being applied, such as the mark 80 labeled "Logo" which stretches and deforms when the secondary strap 72 is stretched and fastened. With this mechanism, users may compare the deformed mark with a picture or illustration included in the product instructions or packaging to determine that the device has been applied correctly.

Figure 10:
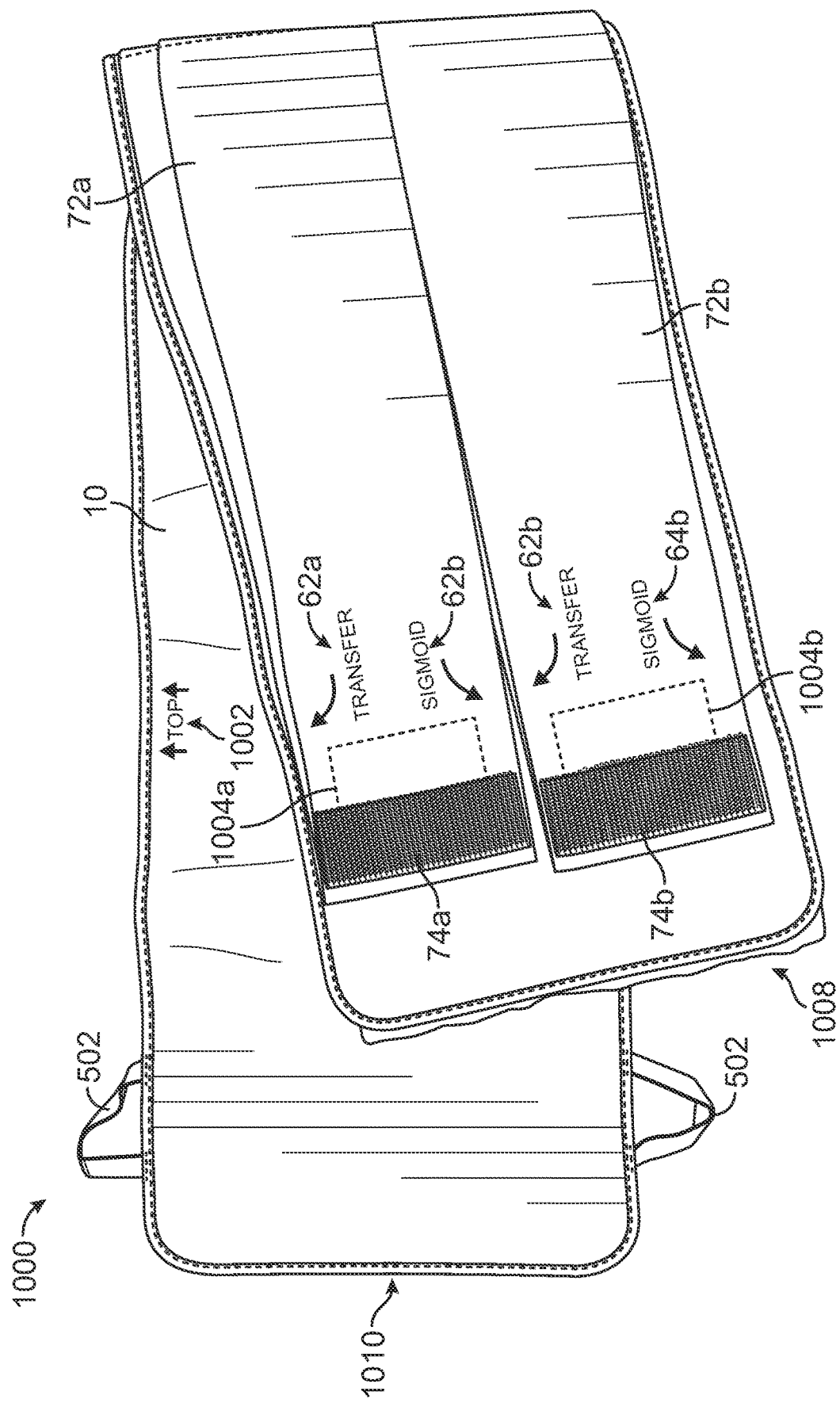
FIG. 10 illustrates an endoscopy band having multiple secondary straps with visual guides for adjusting directional force with the secondary straps.

FIG. 10 illustrates an additional view of a device 1000 including a primary wrap and two elastic secondary straps 72a and 72b. FIG. 10 illustrates that each of the secondary straps 72a and 72b may have a tapered shape and may include a double elastic layer, folded over design, similar to the single strap 72 illustrated in FIG. 4. Alternatively, the two elastic secondary straps 72 and 72b may have a single elastic layer design, such as illustrated for the single strap in FIG. 5. FIG. 10 illustrates an example in which each elastic strap 72a and 72b may include visual indicators showing and/or describing a direction of stretching to apply compression to multiple abdominal areas of a patient, similar to the example for the single strap shown in FIG. 6. For example, the first strap 72a may include a first indicator 62a showing a direction to apply targeted compression to a transverse colon region and a second indicator 64a showing a direction to apply targeted compression to a sigmoid colon region. Similarly, the second strap 72b may include a first indicator 62b showing a direction to apply targeted compression to a transverse colon region and a second indicator 64b showing a direction to apply targeted compression to a sigmoid colon region. FIG. 10 also illustrates stitching 1004a and 1004b, which indicates a placement for a Velcro fastener at the movable end of the two straps 72a, 72b. The closing mechanism 74a, 74b may correspond to a handle that enables the technician to stretch and fasten the elastic straps 72a, 72b more easily. In some aspects, a Velcro fastener may be provided at an interior side of the edge 1008 of the primary wrap, and may be configured to an exterior side of opposite end 1010 of the primary wrap. Thus, the end 1010 may be wrapped under the end 1008 in order to fasten the primary wrap. The handles 502 may be provided on a portion of the primary wrap that is closer to the end 1010, and may be used by a technician to pull the end 1010 further underneath the end 1008 in order to apply a higher level of primary compression through the elastic compression of the primary wrap 10. A visual indicator 1002 may indicate an upper edge of the wrap to assist the direction of placement against the abdomen of a patient.

Figure 11:
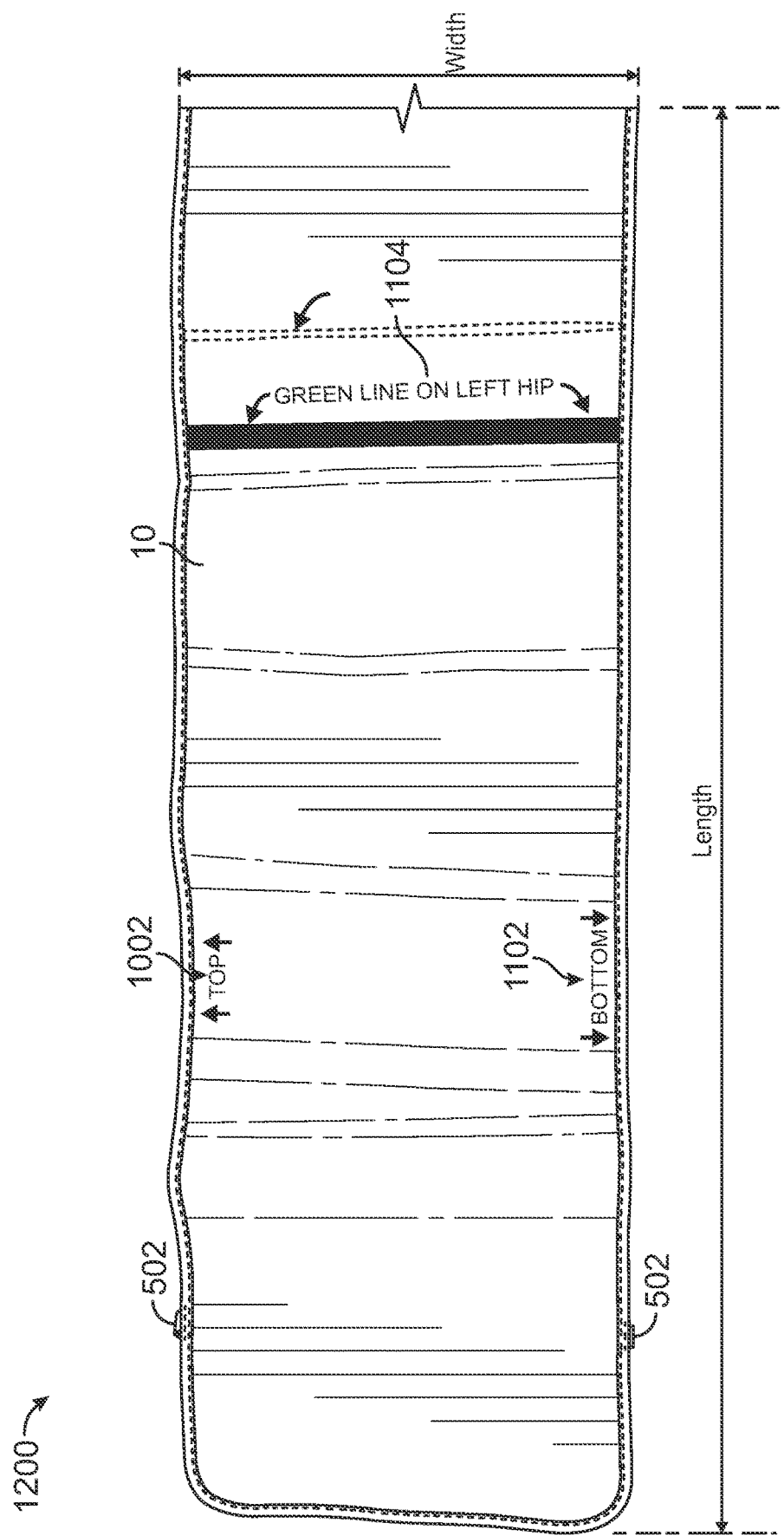
FIG. 11 illustrates an endoscopy band having multiple secondary straps with visual guides for adjusting directional force with the secondary straps.
Figure 12:
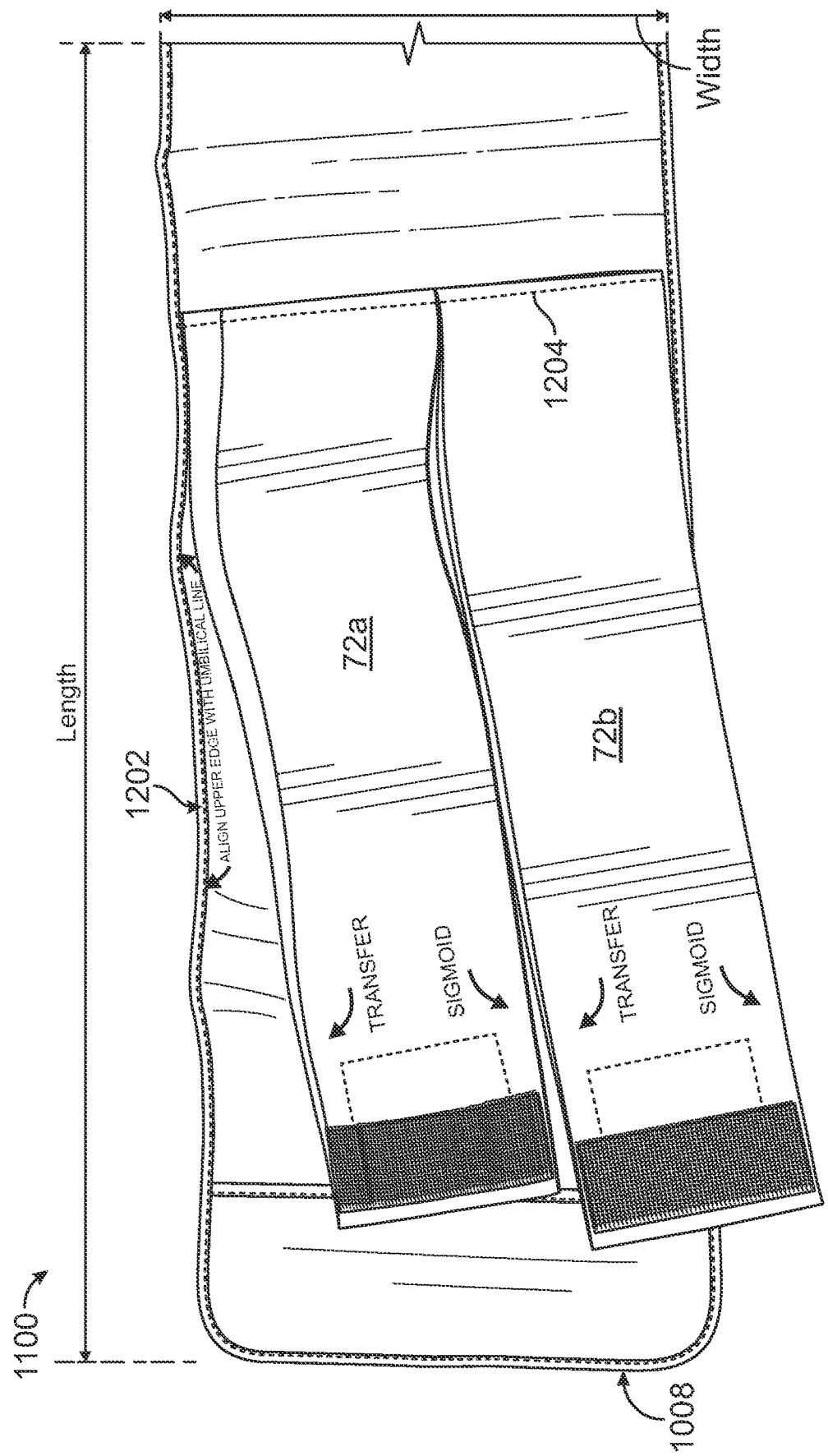
FIG. 12 illustrates an endoscopy band having multiple secondary straps with visual guides for adjusting directional force with the secondary straps.

FIG. 11 shows an interior view 1100 of a primary wrap 10, e.g., a side of the primary wrap that is configured for placement against the patient. In addition to the visual indicator 1002, the primary wrap 10 may further include a visual indicator that indicates a lower or bottom side/edge of the wrap. The top/bottom indicators may be helpful to avoid applying the primary wrap in the opposite direction. If the bottom edge is applied above the top edge, the secondary straps 72a, 72b will extend in the opposite direction and may not provide the targeted compression to the appropriate areas of the patient's abdomen. Additionally, a visual indicator 1104 may be provided to indicate correct placement along a width of the primary band. The example in FIG. 11 provides a line as a visual indicator with respect to the patient's left hip. The indicator may further include one or more arrows and text. Although the example in FIG. 11 uses a green line, the concepts may be applied for an indicator of a different color, a dashed line, a double line, a visual marker that is different than a line, etc. The visual indicator may help a technician to properly place the primary wrap to the patient so that the secondary straps are in the appropriate location to apply targeted compression to particular areas of the abdomen, such as to a sigmoid colon region or to a transverse colon region. FIG. 12 illustrates an exterior view 1200 of a portion of the primary wrap and shows that a visual indicator 1202 may be provided on the exterior of the wrap. In FIG. 12, the visual indicator 1202 assists the technician in placing the primary wrap having the upper edge near the umbilical line. The visual indicator may be placed to line up with a front abdominal region of the primary wrap when the wrap is properly placed (e.g., following the visual indicators on the interior of the primary wrap) and may enable a technician to view the alignment of the visual indicator, e.g., relative to the patient's navel, before or at the time of fastening the closure of the primary wrap. FIG. 12 also illustrates that the straps 72a, 72b may be coupled to the primary wrap at a same position along a length of the primary wrap 10. For example, FIG. 12 illustrates stitching 1204 attaching the fixed end of the straps 72a, 72b to the primary wrap 10.

In some examples, one vertical side of the secondary strap may be fixed to the primary wrap, and the other side may be removably fastened to the primary wrap, such as through a Velcro closure. In other examples, the secondary strap 72 may be fully detachable from the primary wrap, and may have fastening mechanisms at both ends that allow the strap to be secured the exterior side of the primary wrap. The secondary strap in this aspect may be either re-usable or disposable, and may be capable of being stretched and maintaining tension, or may use another mechanism to exert compressive force, when it is secured to the primary band. The strap in this example might not wrap fully around the patient but instead may be stretched directly about the location on the patient's body where force is desired. The strap may be equipped with fastening mechanisms on each end, e.g., to allow the strap to adhere directly to the patient's body.

Improving patient comfort and reducing complications, both during and following endoscopic procedures is very important. Aspects presented herein reduce patient discomfort and complications by helping to prevent and reduce sigmoid looping, which can be a primary cause of patient pain and discomfort.

Patients often become cold or uncomfortably chilled once they change into the garments such as hospital gowns typically worn while undergoing an endoscopic procedure. Many patients request and are provided with blankets, and some facilities provide electric heated blankets, or blankets that have been previously warmed. The heated blankets provide physical warmth, but also they tend to relax the patient and relieve anxiety or discomfort the patient may be experiencing. Aspects presented herein may also help the patient to feel warm and comfortable during the procedure.

The device illustrated in FIGS. 10-12 may include any of the additional aspects described in connection with FIGS. 1-8.

Figure 9:
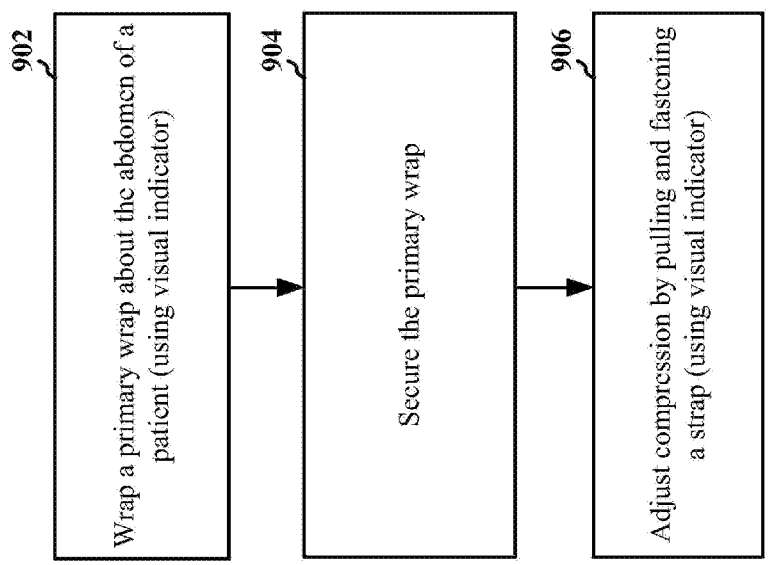
FIG. 9 is a flowchart of an example method of use of an endoscopy band as described herein.

FIG. 9 illustrates aspects of a method for applying pressure and support to a patient's abdomen during advancement of an endoscope during an endoscopy type procedure.

At 902, the method includes wrapping a primary wrap about the abdomen of a patient between the hips and umbilicus of the patient, such as described in connection with FIGS. 2-4. The primary wrap may include any of the aspects described in connection with FIGS. 1-8 and/or 10-12.

At 904, the method includes securing the primary wrap by attaching a first end of the primary wrap to a second portion of the primary wrap after wrapping the primary wrap about the abdomen of the patient.

At 906, the method includes adjusting compression applied to the abdomen of the patient by pulling at least one strap extending from the primary wrap across at least a portion of the primary wrap and to fasten the strap to at least a third portion of the primary wrap, such as illustrated in FIG. 4. The at least one strap may include any of the aspects described in connection with FIGS. 1-8 and/or 10-12. The amount of compression applied to the abdomen of the patient may be adjusted by pulling a strap extending from the primary wrap across at least a portion of the primary wrap at 906 and fastening the strap to the primary wrap. The strap may be coupled to a portion of the primary wrap that is configured for placement over a left side of the subject's lower abdomen. This allows the patient's own body weight to be leveraged in order to adjust the compression provided by the strap. The strap may be configured to be pulled in a direction toward a right side of the subject's lower abdomen to adjust the amount of pressure applied by the endoscopy support apparatus. A combination of visual indicators may enable correct placement of the device on a patient and may assist in applying targeted compression through adjustment of the at least one strap. The at least one visual indicator may include any of the aspects described in connection with FIGS. 1-8 and/or 10-12.

The primary wrap is placed relative to the abdomen of the patient and/or the strap is extended using at least one visual indicator. The at least one visual indicator may include a visual indication of a direction of stretching the at least one elastic band to apply the additional targeted force to a sigmoid region of the subject, such as described in connection with the examples in FIGS. 6 and 8. The visual indication may include an arrow illustrating the direction and/or text indicating the sigmoid region. Thus, at 906, the method may include using the visual indication to adjust the strap to apply targeted force to the sigmoid colon of the subject.

The at least one visual indicator may include a visual indication of a direction of stretching the at least one elastic band to apply the additional targeted force to a traverse colon region of the subject, such as described in connection with the examples in FIGS. 6 and 8. The visual indication may include an arrow illustrating the direction and/or text indicating the transverse colon region. Thus, at 906, the method may include using the visual indication to adjust the strap to apply targeted force to the transverse colon of the subject.

The at least one visual indicator may include a visual indication on the primary wrap indicating placement of the primary wrap relative to the abdomen of the subject, such as described in connection with FIG. 7. Thus, at 902, the method may include using the visual indication to place the primary wrap relative to the abdomen of the subject.

The visual indication may indicate that an edge extending the length of the primary wrap is to be placed at an umbilical line of the subject, such as described in connection with FIG. 7. The visual indication may include an arrow indicating the edge of the wrap and/or text indicating describing that the edge is for placement at an umbilical line of the subject. Thus, at 902, the method may include using the visual indication to place an edge of the primary wrap relative aligned with the umbilical line of the subject.

The at least one visual indicator may include a visual indication on the primary wrap indicating placement of the primary wrap relative to a left hip of the subject, such as described in connection with FIG. 7. For example, the visual indication may indicate an alignment of the fixed end of the secondary strap with the left hip of the subject. The visual indication may include an arrow indicating the fixed end of the secondary strap, contrasting stitching that fixes the fixed end of the secondary strap to the primary wrap, and/or text indicating describing that the placement relative to the left hip of the subject. Thus, at 902, the method may include using the visual indication to place an edge of the primary wrap relative to the left hip of the subject.

At 906, the compression may be adjusted for multiple target locations through the adjustment of more than one strap. For example, as described in connection with FIG. 8, the user may adjust compression at a first abdominal region by stretching and fastening a first elastic strap and may adjust compression at a second abdominal region by stretching and fastening a second elastic strap. The multiple elastic straps may include visual indicators indicating a direction of stretching to apply targeted compression to different regions of a colon, e.g., to a sigmoid region and/or a transverse region. The use of multiple secondary straps enables simultaneous targeted compression of different abdominal areas, e.g., different regions of a colon during an endoscopy procedure.

To additionally enhance patient comfort, certain aspects of the invention are designed to be single-use, and to remain fastened in place on the patient during the procedure and/or following the procedure. For example, maintaining the compression applied by the device during the withdrawal phase of the procedure and while imaging is performed may help improve the detection of adenoma. The device may be maintain on the patient to reduce the common post-procedure complications of bloating and abdominal pain caused by bloating. Otherwise known as gaseous distention, bloating occurs following endoscopy procedures because physicians often use compressed air or carbon dioxide to insufflate parts of the bowel that are difficult to see and examine. The gas opens up the area to allow for a more complete visualization, enhancing the efficacy of the procedure. However, the gas also remains in the patient until it is either absorbed or expelled. Expulsion is the primary gas removal mechanism as absorption is a very inefficient process. Gaseous distention is a primary post-procedure complication and a frequent complaint from patients. However when the wrap described herein remains in place after the procedure, the lower abdominal compression generated by the device allows the bowel to more rapidly evacuate trapped by directing excess gas towards the rectum. As a result, the severity and duration of post-procedure bloating and associated abdominal pain may be reduced.

The contents of each of U.S. application Ser. No. 15/256,019, entitled "METHOD AND APPARATUS FOR ENHANCED VISUALIZATION DURING ENDOSCOPY," and filed on Sep. 2, 2016; U.S. Application Ser. No. 13/344,715, entitled "METHOD AND APPARATUS FOR TENSILE COLONOSCOPY COMPRESSION," and filed on Jan. 6, 2012; U.S. application Ser. No. 14/575,860, entitled "ENDOSCOPY BAND WITH SIGMOID SUPPORT APPARATUS," and filed on Dec. 18, 2014; U.S. Provisional Application Ser. No. 61/917,469, entitled "COLONOSCOPY BAND WITH SIGMOID SPLINT" and filed on Dec. 18, 2013; U.S. Provisional Application Ser. No. 61/944,658 entitled "ENDOSCOPY BAND WITH SIGMOID SUPPORT APPARATUS" and filed on Feb. 26, 2014; U.S. Provisional Application No. 62/214,747, entitled "IMPROVED BOWEL STABILITY AND ENHANCED VISUALIZATION DURING ENDOSCOPY" and filed on Sep. 4, 2015, are expressly incorporated by reference herein in their entirety.

Example aspects of the present invention have now been described in accordance with the above advantages. It will be appreciated that these examples are merely illustrative of aspects of the present invention. Many variations and modifications will be apparent to those skilled in the art.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects." Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

The invention claimed is:

1. An endoscopy support apparatus, comprising:
 a primary wrap comprising a band of elastic material sized for placement around a lower abdomen of a subject;
 a closing mechanism provided at an end of the primary wrap to secure the primary wrap around an abdomen of the subject by removably attaching the end of the primary wrap to a second portion of the primary wrap;
 at least one elastic strap having a first end fixed to the primary wrap and a second end comprising a coupling mechanism for removably coupling the second end to the primary wrap, wherein the at least one elastic strap is configured to be placed with the first fixed end at a left hip of the subject and to extend in a left to right direction across a front abdomen portion of the primary wrap in order to exert an additional targeted force between the first end and the second end, wherein the additional targeted force is targeted to at least one of a sigmoid region or a transverse colon region of the abdomen of the subject; and
 at least one visual indicator provided on the primary wrap or the at least one elastic strap that indicates a direction of adjustment of the at least one elastic strap for targeted compression, wherein the at least one visual indicator includes:
  a sigmoid text label and a first arrow indicating a first direction to apply the targeted compression to the sigmoid region, and
  a transverse text label and a second arrow indicating a second direction to apply the targeted compression to the transverse colon region, the first direction being different than the second direction.

2. The endoscopy support apparatus of claim 1, wherein the at least one elastic strap comprises:

a first elastic strap extending in the left to right direction from the primary wrap for application of the targeted compression to a first abdominal region of the subject, wherein the sigmoid text label and the first arrow are located on the first elastic strap; and a second elastic strap extending from the primary wrap extending in the left to right direction for the application of the targeted compression to a second abdominal region of the subject, wherein the transverse text label and the second arrow are located on the second elastic strap.

3. The endoscopy support apparatus of claim 2, wherein the primary wrap comprises:

an upper edge for the placement relative to an umbilical line of the subject; and a lower edge for the placement below the umbilical line of the subject, wherein the first elastic strap and the second elastic strap extend from the primary wrap at a same position along a length of the primary wrap, and wherein the first elastic strap extends from a first position along a width of the primary wrap and the second elastic strap extends from a second position along the width of the primary wrap, the second position being closer to the upper edge than the first position.

4. The endoscopy support apparatus of claim 1, wherein the first arrow indicates the direction of stretching the at least one elastic strap to apply the additional targeted force to the sigmoid region of the subject.

5. The endoscopy support apparatus of claim 1, wherein the second arrow indicates the direction of stretching the at least one elastic strap to apply the additional targeted force to the transverse colon region of the subject.

6. The endoscopy support apparatus of claim 1, further include at least one additional visual indicator on the primary wrap indicating the placement of the primary wrap relative to the abdomen of the subject.

7. The endoscopy support apparatus of claim 6, wherein the at least one additional visual indicator indicates that an edge extending a length of the primary wrap is to be placed at an umbilical line of the subject.

8. The endoscopy support apparatus of claim 7, wherein the at least one additional visual indicator includes an additional arrow indicating the edge of the primary wrap.

9. The endoscopy support apparatus of claim 8, wherein the at least one additional visual indicator further includes text indicating the placement relative to the left hip of the subject.

10. The endoscopy support apparatus of claim 7, wherein the at least one additional visual indicator includes text indicating that the edge is for the placement at the umbilical line of the subject.

11. The endoscopy support apparatus of claim 1, further including at least one additional visual indicator on the primary wrap indicating the placement of the primary wrap relative to a hip of the subject.

12. The endoscopy support apparatus of claim 11, wherein the at least one additional visual indicator indicates an alignment of the first end of the at least one elastic strap with the hip of the subject.

13. The endoscopy support apparatus of claim 12, wherein the at least one additional visual indicator further includes an additional arrow indicating the first end of the at least one elastic strap.

14. The endoscopy support apparatus of claim 12, wherein the at least one additional visual indicator further includes contrasting stitching that fixes the first end of the at least one elastic strap to the primary wrap.

15. The endoscopy support apparatus of claim 1, wherein the at least one visual indicator includes:

a first visual indication on a first side of the primary wrap including first text and and additional arrow visually showing a user one edge extending a length of the primary wrap that is to be placed at an umbilical line of the subject, and a second visual indication on the first side of the primary wrap and including second text and a line indicating an alignment of a hip of the subject with the first end of the at least one elastic strap that is fixed on a second side of the primary wrap.

16. The endoscopy support apparatus of claim 1, wherein the at least one elastic strap comprises:

a first elastic strap extending in the left to right direction from the primary wrap for application of the targeted compression to a first abdominal region of the subject, wherein the first elastic strap includes:

the sigmoid text label and the first arrow that indicate the first direction to apply the targeted compression to the sigmoid region via the first elastic strap; and the transverse text label and the second arrow that indicate the second direction to apply the targeted compression to the transverse colon region via the first elastic strap; and a second elastic strap extending from the primary wrap extending in the left to right direction for the application of the targeted compression to a second abdominal region of the subject, wherein the second elastic strap includes:

a second sigmoid text label and a third arrow that indicate the first direction to apply the targeted compression to the sigmoid region via the second elastic strap; and a second transverse text label and a fourth arrow that indicate the second direction to apply the targeted compression to the transverse colon region via the second elastic strap.

17. A method for applying pressure to an abdomen of a patient to apply constant pressure and support to the abdomen during advancement of an endoscope during an endoscopy, comprising:

wrapping a primary wrap about the abdomen of the patient between a hip level and umbilicus of the patient with a first end of at least one elastic strap that is fixed to the primary wrap at a left hip of the patient;

securing the primary wrap by attaching a first end of the primary wrap to a second portion of the primary wrap after wrapping the primary wrap about the abdomen of the patient; and adjusting a targeted compression applied to the at least one of a sigmoid region or a transverse colon region of the abdomen of the patient by pulling the at least one elastic strap extending from the first end, which is fixed to the primary wrap, across at least a portion of the primary wrap and to fasten the at least one elastic strap to a third portion of the primary wrap, wherein the targeted compression is adjusted by extending the at least one elastic strap in a direction indicated by at least one visual indicator on the at least one elastic strap, wherein the at least one visual indicator includes:

a sigmoid text label and a first arrow indicating a first direction to apply the targeted compression to the sigmoid region, and a transverse text label and a second arrow indicating a second direction to apply the targeted compression to the transverse colon region, the first direction being different than the second direction.

18. The method of claim 17, wherein the at least one elastic strap that is adjusted comprises a first elastic strap extending in a left to right direction from the primary wrap for application of the targeted compression to a first abdominal region of the patient, wherein the sigmoid text label and the first arrow are located on the first elastic strap and a second elastic strap extending from the primary wrap extending in the left to right direction for the application of the targeted compression to a second abdominal region of the patient, wherein the transverse text label and the second arrow are located on the second elastic strap.

19. The method of claim 17, further comprising:
placing the primary wrap relative to the abdomen of the patient in alignment with at least one additional visual indicator provided on the primary wrap that indicates placement of the primary wrap relative to the abdomen of the patient.

20. The method of claim 19, wherein placing the primary wrap relative to the abdomen of the patient includes aligning an edge extending a length of the primary wrap with the at least one additional visual indicator that indicates that the edge extending the length of the primary wrap is to be placed at an umbilical line of the patient, wherein the at least one additional visual indicator includes one or more of an additional arrow indicating the edge of the primary wrap or text indicating that the edge is for the placement at the umbilical line of the patient.

21. The method of claim 19, wherein placing the primary wrap relative to the abdomen of the patient includes placing the first end of the at least one elastic strap to align with a hip of the patient based on the at least one additional visual indicator that includes one or more of:
an additional arrow indicating the first end of the at least one elastic strap, contrasting stitching that fixes the first end of the at least one elastic strap to the primary wrap, or text indicating the placement relative to the left hip of the patient.

* * * * *